United States Patent
Kalender et al.

(10) Patent No.: US 7,283,606 B2
(45) Date of Patent: Oct. 16, 2007

(54) METHOD FOR RECONSTRUCTING PROJECTION DATA SETS FOR DOSE-REDUCED SECTIONAL SPIRAL SCANNING IN COMPUTED TOMOGRAPHY

(75) Inventors: Willi Kalender, Möhrendorf (DE); Stefan Schaller, Fürth (DE); Bernhard Schmidt, Malvern, PA (US)

(73) Assignee: Siemens Aktiengesellschaft, Munich (DE)

(*) Notice: Subject to any disclaimer, the term of this patent is extended or adjusted under 35 U.S.C. 154(b) by 55 days.

(21) Appl. No.: 11/116,196

(22) Filed: Apr. 28, 2005

(65) Prior Publication Data

US 2005/0254621 A1 Nov. 17, 2005

(30) Foreign Application Priority Data

Apr. 28, 2004 (DE) ...................... 10 2004 020 861

(51) Int. Cl.
- *H05G 1/60* (2006.01)
- *H05G 1/64* (2006.01)
- *A61B 6/03* (2006.01)

(52) U.S. Cl. .................. 378/8; 378/15; 378/16; 378/108

(58) Field of Classification Search ............ 378/4, 378/15, 16, 108–112, 8
See application file for complete search history.

(56) References Cited

U.S. PATENT DOCUMENTS

| | | | |
|---|---|---|---|
| 5,867,555 A | 2/1999 | Popescu et al. ............... 378/16 |
| 5,873,826 A | 2/1999 | Gono et al. .................. 600/425 |
| 6,298,111 B1* | 10/2001 | Ozaki ............................. 378/8 |
| 6,381,297 B1* | 4/2002 | Hsieh ........................... 378/15 |
| 6,400,789 B1* | 6/2002 | Dafni ........................... 378/15 |
| 6,452,996 B1* | 9/2002 | Hsieh ........................... 378/15 |
| 6,463,118 B2* | 10/2002 | Besson ......................... 378/15 |
| 6,597,803 B1* | 7/2003 | Pan et al. .................... 382/131 |
| 6,628,742 B2* | 9/2003 | Pan et al. ....................... 378/8 |
| 6,744,846 B2 | 6/2004 | Popescu et al. ............... 378/16 |
| 6,775,352 B2* | 8/2004 | Toth et al. ................... 378/108 |
| 6,826,251 B1* | 11/2004 | Miyazaki et al. ............. 378/15 |

(Continued)

OTHER PUBLICATIONS

"Dose Reduction in CT by Anatomically Adapted Tube Current Modulation," Kalender et al, Med. Phys. 26, vol. 11 (Nov. 1999) pp. 2248-2253.

(Continued)

*Primary Examiner*—Allen C. Ho
(74) *Attorney, Agent, or Firm*—Schiff Hardin LLP

(57) ABSTRACT

In a method and CT apparatus and software product for reconstructing incomplete projection data sets for dose-reduced sectional spiral scanning along a z axis of a patient on a table that is movable in the z direction in the CT apparatus that has a radiation source supplied with tube current so as to emit a beam that strikes a detector system to obtain scanning data from which in an image computing device generates two-dimensional and three-dimensional scanning images of the examination subject, at a pitch greater or equal to one. For z positions having an incomplete projection data set for reconstruction of the image, in a preprocessing step data from another row of this projection and/or data for a previous or subsequent 360° rotation are used to compute a complete projection data set therefor.

8 Claims, 4 Drawing Sheets

U.S. PATENT DOCUMENTS

| | | |
|---|---|---|
| 6,850,588 B2 * | 2/2005 | Arenson et al. ............... 378/16 |
| 6,853,701 B2 | 2/2005 | Cherek et al. ................. 378/16 |
| 6,865,250 B2 * | 3/2005 | Londt et al. .................... 378/8 |
| 6,873,676 B2 * | 3/2005 | Hsieh ............................ 378/4 |
| 6,987,828 B2 * | 1/2006 | Horiuchi ....................... 378/16 |
| 2005/0058249 A1 | 3/2005 | Wolf et al. ................. 378/109 |

OTHER PUBLICATIONS

ICRP Publication 80 "Recommendations of the International Commission on Radiological Protection," (1990).

ICRP Publication 87 "Managing Patient Dose in Computed Tomography," Valentin (ed.) (Dec. 2000).

* cited by examiner

Pitch < 1     Projection angle a.p.

Pitch = 1     Projection angle a.p.

Pitch > 1     Projection angle a.p.

METHOD FOR RECONSTRUCTING PROJECTION DATA SETS FOR DOSE-REDUCED SECTIONAL SPIRAL SCANNING IN COMPUTED TOMOGRAPHY

BACKGROUND OF THE INVENTION

1. Field of the Invention

The present invention relates in general to computed tomography as used in medicine to examine patients, particularly to a method for image reconstruction for sectional dose-reduced spiral scanning.

2. Description of the Prior Art

Using modern medical diagnostic techniques such as X-ray computed tomography, it is possible to acquire image data for an object to be examined. The examined object is generally a patient.

X-ray computed tomography (CT for short) is an X-ray imaging technique that differs fundamentally in terms of the image formation from classic X-ray tomographic imaging techniques. With CT images, transverse image slices are obtained, i.e., images of body slices that are oriented essentially perpendicularly to the body axis. The tissue-specific physical quantity represented in the image is the distribution of the attenuation values of X-ray radiation $\mu(x, y)$ in the slice plane. The CT image is obtained by reconstruction from the two-dimensional distribution of $\mu(x, y)$ from numerous different angles of view (projections).

The projection data are determined from the intensity I of an X-ray beam after passing through the slice to be imaged and from its original intensity IO at the X-ray source according to the absorption law as follows:

$$\ln \frac{I_0}{I} = \int_L \mu(x, y) dl$$

The integration path L represents the path of the observed X-ray beam through the two-dimensional attenuation distribution $\mu(x, y)$. An image projection is then composed of the measured values that were acquired with the X-ray beams for a viewing direction of the line integrals through the object slice.

The projections emanating from a wide variety of different directions (characterized by the projection angle $\Phi$) are obtained using a combined X-ray tube detector system (gantry) that rotates in the slice plane about the object. The most commonly used devices currently are the type is known as "fan-beam devices" in which a tube and an array of detectors (a linear arrangement of detectors with a defined width S) rotate in the slice plane jointly about a rotational center which is also the middle of the circular measurement field. "Parallel radiation devices" are also known, but exhibit very long measurement times are not explained in detail herein. It must be noted, however, that a transformation of fans—to parallel projections and vice versa—is possible so that the present invention that is to be explained based on a fan-beam device is equally applicable for parallel-beam devices.

FIG. 6 schematically shows a computed tomography device for a fan-beam technique. In this device, an X-ray tube 7 and a radiation receiver 13 (an array of linearly arranged detector elements) rotate—the two together being known as a "gantry"—jointly around a rotational center which is also the center of the circular measurement field 5 (gantry opening) and in which the patient to be examined 1 is located on a patient bed 2. In order to be able to examine different parallel planes of patient 1, the patient bed can be displaced along the body's longitudinal axis. As can be seen from FIG. 6, in CT imaging transversal image slices will result, i.e. images of body slices oriented essentially perpendicularly to the bodily axis. CT requires projections at many angles $\phi$. To generate a slice image, the beam cone emitted by the X-ray tube 7 is gated such that a planar radiation fan arises which traces one-dimensional central projections of the irradiated slice. For exact reconstruction of the distribution of the attenuation values $\mu z(x, y)$ (where z is the position on the body's longitudinal axis), this radiation fan must be perpendicular on the rotation axis and also must be spread wide enough to completely cover, from each projection direction $\phi$, the slice of the measurement object in the beam's field of view. The radiation fan penetrating the object is detected by detectors that are linearly arranged on a circle segment. With conventional devices, there are up to 1000 detectors. The individual detector responds to the incident beams with electrical signals the amplitude of which is proportional to the intensity of these beams. With detectors known as "multi-row detectors", a number of detector rows are arranged in parallel.

Each individual detector signal belonging to a projection $\phi$ is picked up in each case by an electronic measurement circuit 15 and forwarded to a computing unit (computer or system computer) 16. With the computing unit 16, the measured data can now be processed in a suitable manner and displayed in the form of an X-ray image in units known as "Hounsfield units" on a monitor 14.

Larger volumes of the examination subject generally are picked up using spiral scanning (spiral scan). With spiral scanning, the gantry rotates with the radiation source continuously around the examination subject while the patient bed is displaced relative to the gantry continuously along a system axis (generally the patient's longitudinal axis, or z axis).

The radiation source thus delineates, referenced to the examination subject, a spiral path until the volume determined prior to the examination has been scanned. Based on the spiral data acquired in this manner, images for the individual slices then can be computed.

The parameter selection in spiral CT corresponds largely to that used in conventional CT.

As an additional parameter in spiral scans, the table feed d in mm per 360° rotation must be selected. The ratio of the table feed d to the slice collimation M·S (the product of the number M of detector rows and the width S of the detector row) as a dimensionless quantity is generally referred to as the pitch or pitch factor p:

$$p = \frac{d}{M \cdot S}$$

Generally, pitch values between 1 and 2 are chosen. The larger the pitch, the faster the scan volume is covered.

As a general rule, the patient dose depends both in conventional CT and in spiral CT on many parameters, besides the technical properties of the CT system and the selected examination parameters, particularly also on the patient size and the selected anatomical examination region.

Because CT imaging is based on the attenuation or absorption of X-ray radiation in organic tissue, during the irradiation an energy transfer to tissue results (radiation dose), which can lead to cell damage.

A goal in CT imaging is to keep the dose during the CT imaging as low as possible for the patient. Particularly, it is important to ensure that particularly radiation-sensitive organs receive as little exposure as possible. According to "ICRP: Publication 60—Recommendation of the International Commission on Radiological Projection; Pergamon Press, Oxford, 1990", particularly radiation-sensitive organs include, i.e., the gonads, female mammary gland, thyroid gland and the eye lens.

Conventionally, the dose for the patient in CT imaging usually is reduced, for example, by reducing the tube current. A simple reduction in the tube current reduces the dose for the patient, but the image quality is degraded to the same extent.

The influence of a dose reduction on the image quality cannot be ignored. A dose reduction technique that has been further developed in this regard involves an attenuation-dependent tube current modulation (CAREDose, Gies, Kalender, Wolf, Suess: Dose reduction in CT by anatomically adopted tube current modulation, 1 Simulation Studies Med. Phys. 26 (11): 2231-2247, 1999). In this technology, for projections with a high attenuation—e.g., laterally along the shoulder axis of the patient—the tube current is slightly boosted; for projections with a low attenuation—e.g., from anterior to posterior (a.p.) or vice versa (p.a.)—the tube current is greatly reduced. Use is made of the fact that the image point noise is determined primarily by the projections in which the attenuation through the object is high. A reduction of the tube current in the projections with low attenuation thus has no negative influence on the image quality.

CT fluoroscopy proceeds in a similar manner, wherein data are continuously acquired and immediately reconstructed from the same slice. The imaging takes place without any movement of the table. In this manner, it is possible to track the position of a medical instrument in the patient, for example, in the context of a centesis or biopsy. A current image is always available to the physician performing the examination. To protect the hand of the physician from excessive radiation exposure, in a special embodiment of fluoroscopy (HandCARE), the X-ray radiation is greatly reduced, or switched off totally, in the anterior-posterior direction. This method (HandCARE) thus aims to minimize the radiation dose to the physician, i.e., the dose to the hand of the physician. The missing data for projections with reduced or missing radiation are reconstructed in HandCARE using suitable algorithms.

As already mentioned, the data acquisition takes place in the described techniques in a slice-by-slice manner without selective dose reduction.

SUMMARY OF THE INVENTION

An object of the present invention is to provide a fast CT volume imaging and reconstruction technique that allows an intentional radiation dose reduction to be made for organs that are particularly sensitive to radiation.

This object is achieved according to the invention by a method for reconstructing incomplete projection data sets for dose-reduced sectional spiral scanning along the z axis of a patient lying on a table that is movable in the z direction using a CT device with a radiation source supplied with a tube current that emits a beam that strikes a detector system to provide scanning data based on which, in an image computing device, two-dimensional and three-dimensional scanning images of the examination subject are determined, at a pitch greater or equal to one. For z positions with an incomplete projection data set for reconstruction of the image, at such a z position, in a preprocessing step, data form another row of this projection and/or data for a previous or subsequent 360° rotation are used to compute a complete projection data set therefor.

The computation of the complete projection data set can take place according to the invention by interpolation. Preferably the interpolation takes place in a linear manner.

Particularly for a pitch equal to one, in an embodiment of the invention for reconstruction of an image at a z position between two radiation segments, a re-sorting of data from adjacent rotations is carried out.

The dose reduction can take place in an anterior manner and particularly in an angular range of $\beta=180°-\alpha$, where $\alpha$ is the fan angle of the radiation source.

The dose reduction in another embodiment of the invention takes place by switching off the tube current in the dose-reduced section.

The above object also is achieved, according to the invention by an apparatus is claimed for implementing the method described above.

The above object also is achieved according to the invention by a computer software product that implements the method described above by running in a computing unit connected to a CT device.

DESCRIPTION OF THE PREFERRED EMBODIMENTS

Figure 1:
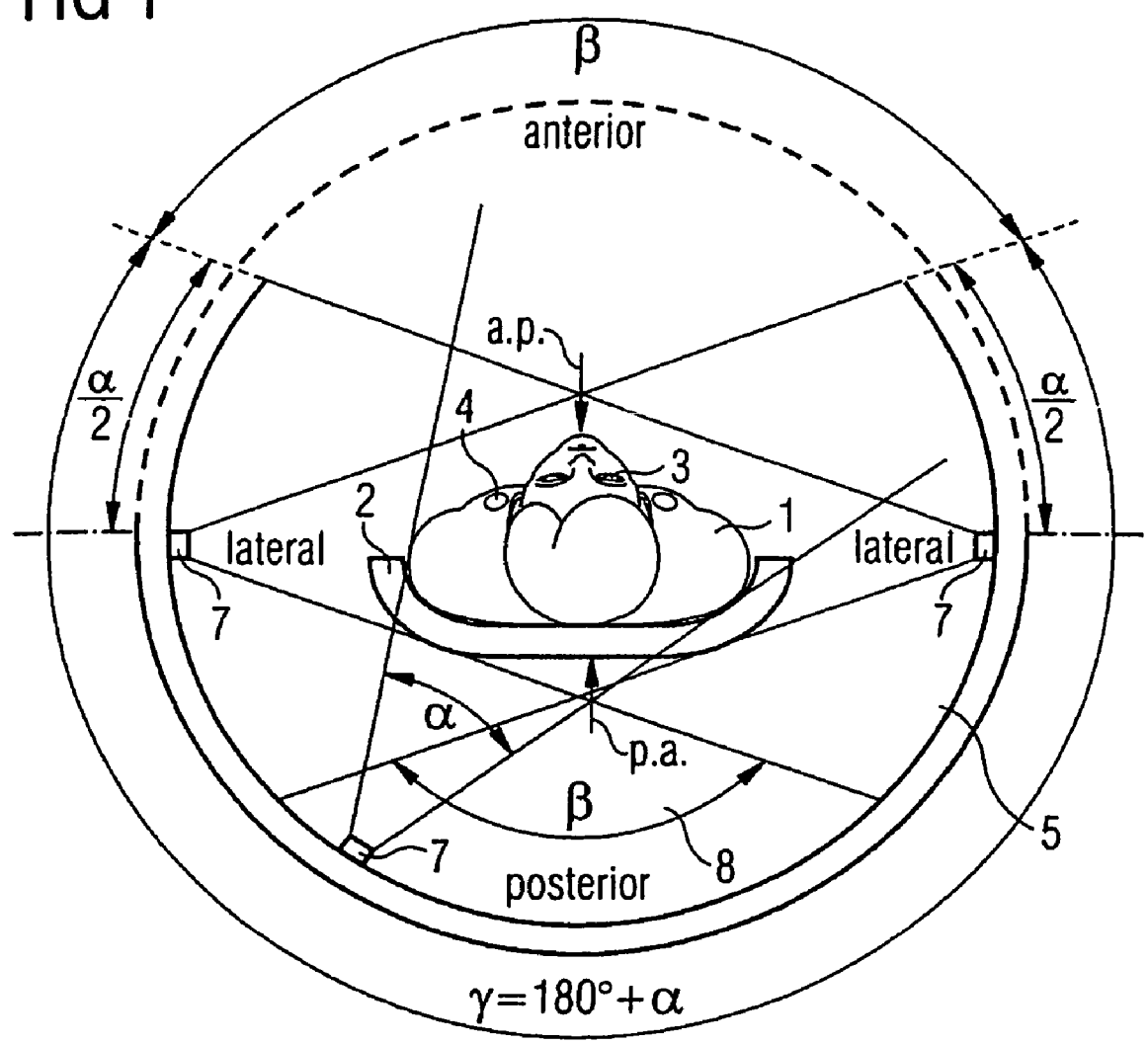
FIG. 1 schematically illustrates, in a front view, the angular relationships of the projections for the scanning method according to the invention.
Figure 2:
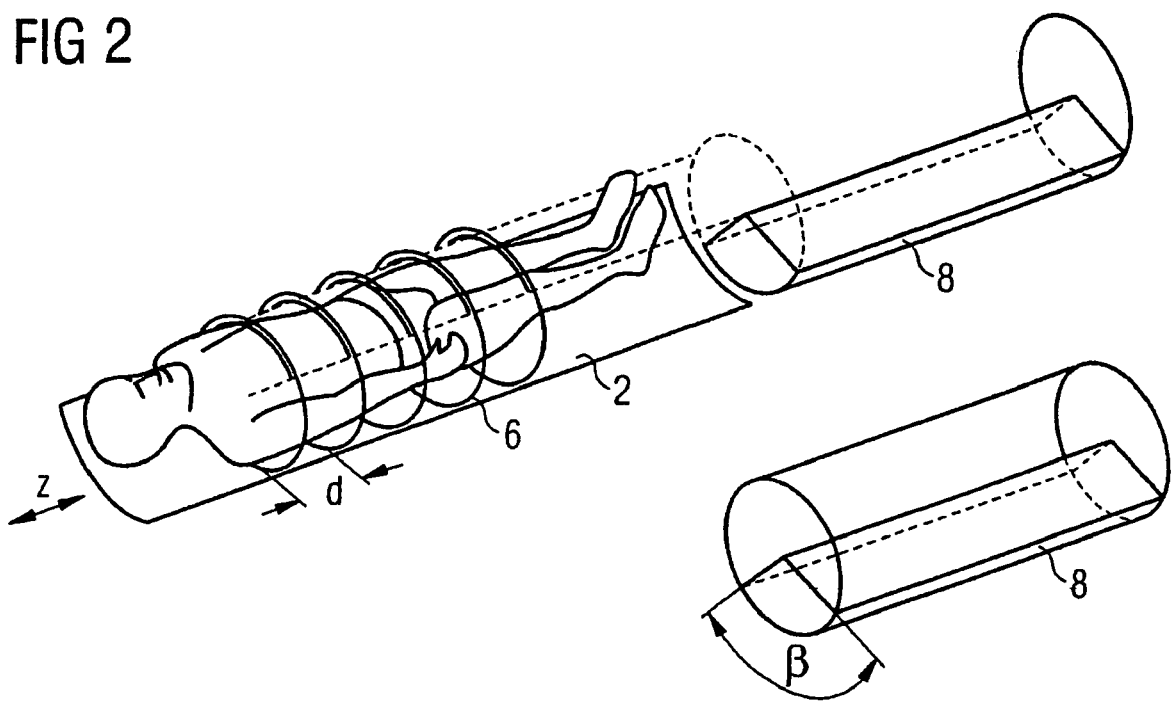
FIG. 2 schematically illustrates, in a perspective manner, the spiral tracks of the scanning caused by the table feed d along the patient's longitudinal axis z.

FIG. 1 schematically shows, in a front view, a patient 1 on a patient bed 2. The patient 1 lies on his or her back so that radiation-sensitive organs (such as the mammary glands 4 and the eye lens 3) are facing the upper area (anterior) of the gantry opening 5. The scanning takes place such that the X-ray tube detector unit (gantry) rotates in a circular manner around the patient 1 while the patient 1 is moved at a uniform speed (constant table feed d) along the patient's longitudinal axis z. The combination of the gantry rotation and the patient displacement results in, as shown in FIG. 2, a spiral-shaped or helix-shaped scanning trajectory 6 as is conventional in spiral CT.

An object of the present invention is, within the context of spiral scanning, to protect the aforementioned radiation-sensitive organs, or to expose them to the lowest possible radiation dose for the best possible image quality (minimal information loss). According to the invention, this is achieved by the X-ray tube being supplied with current exclusively in the lower region of the gantry opening over an angular range $$\gamma = 180° + \alpha.$$

The geometric situation is as follows: The patient 1 lies in the middle of the gantry opening 5. It is divided by the shoulder axis of the patient 1 (lateral projection) horizontally into two halves. The upper half is known as the anterior region while the lower half is known as the posterior region. If radiation propagates from anterior to posterior, this is an a.p. projection, and if radiation propagates from posterior to anterior, this is a p.a. projection.

According to the invention, radiation is emitted (activated) only in the angular range $\gamma = \alpha/2 + 180° + \alpha/2 = 180° + \alpha$ (in other words, laterally and p.a.), the fan angle $\alpha$ of the X-ray tube 7 being selected so that the patient 1 is completely irradiated at each projection angle of the X-ray tube, and thus by the radiation fan, from the lower half ($\gamma = \alpha/2 + 180° + \alpha/2$, lateral and p.a.).

For tube positions in the a.p. region ($\beta = 180° - \alpha$, indicated by the dashed line in the upper half of the gantry opening 5), no radiation is emitted according to the invention. This means that radiation still is emitted in lateral projections or for lateral positions of the radiation source, so that overall, per 360° rotation, projection data are acquired in a range of $\gamma = 2 \cdot \alpha/2 + 180°$ (in other words, from 180° plus the fan angle). In this manner, the a.p. side of the patient is spared and the dose for radiation-sensitive organs (e.g., gonads, mammary gland, thyroid gland and eye lens) that lie primarily on the a.p. side is significantly reduced.

Figure 5:
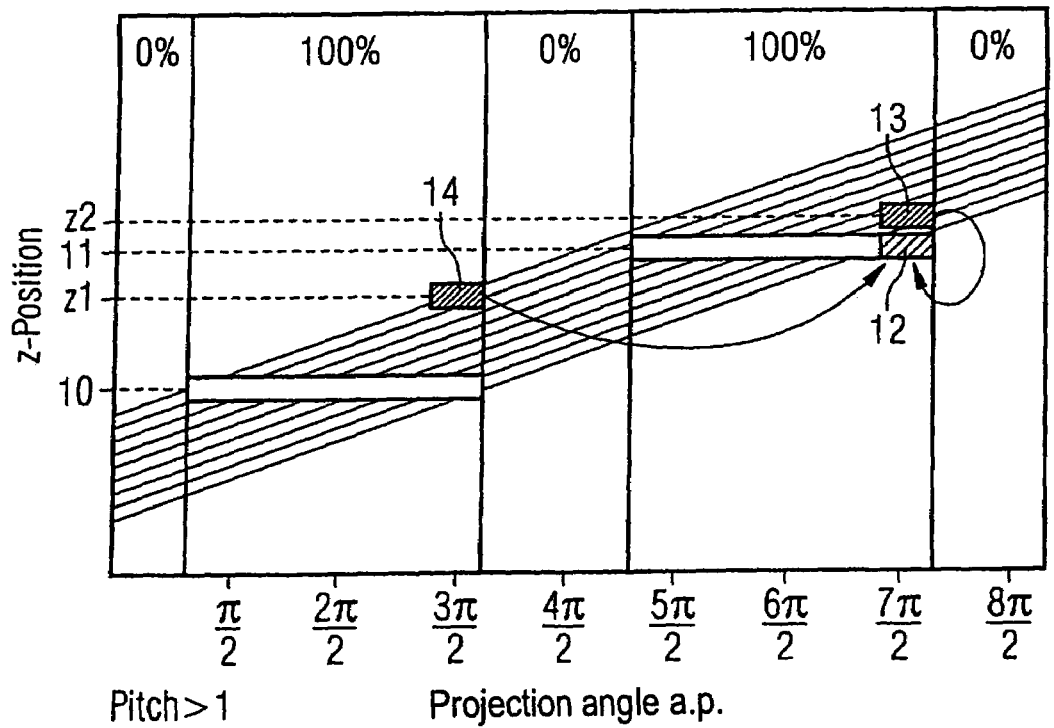
FIG. 5 schematically illustrates the data that the multi-row detector detects when the X-ray tube is switched on and the pitch factor is greater than 1.
Figure 6:
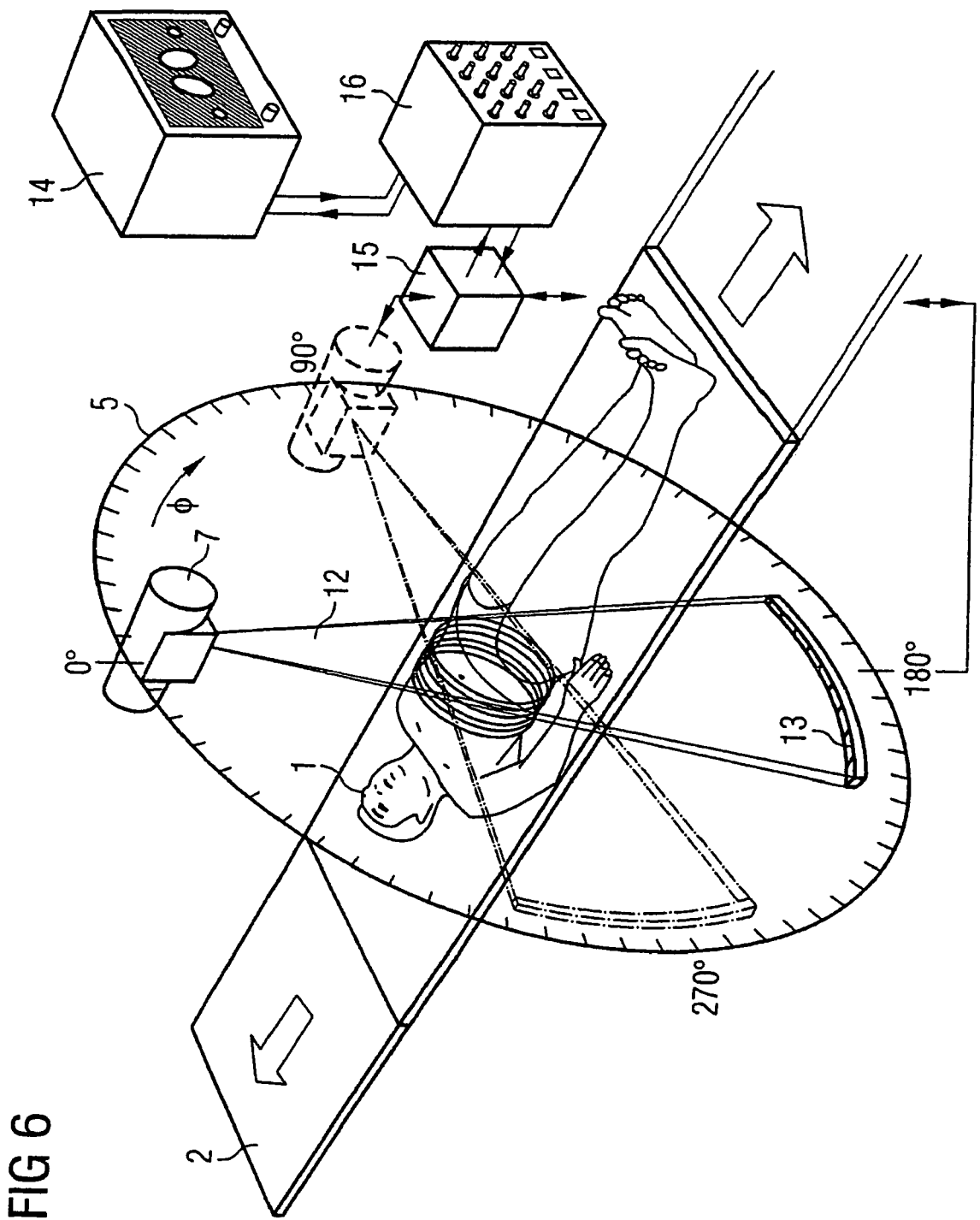
FIG. 6 schematically illustrates a computed tomography apparatus constructed and operating in accordance with the invention.

This limitation of the irradiation or projection region to the p.a. region thus has the consequence that in a range on the p.a. side of $\beta = 180° - 2 \cdot \alpha/2 = 180° - \alpha$, which represents an obtuse-angled cylinder sector 8 along the entire spiral, no measured values exist. Missing values in this range can be reconstructed as is illustrated in FIG. 5. According to the invention, the reconstruction algorithm is part of a computer software product that is executed by the computing unit 16 connected to the CT apparatus (cf. FIG. 6).

Figure 3:
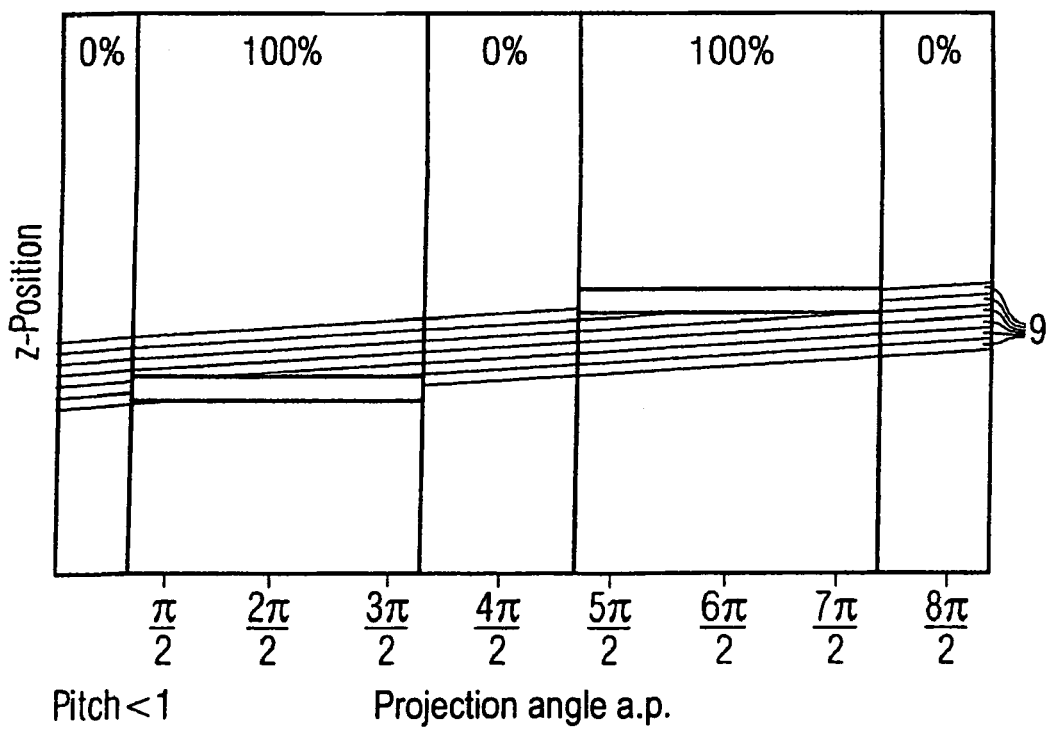
FIG. 3 schematically illustrates the data that the multi-row detector detects when the X-ray tube is switched on and the pitch factor is less than 1.
Figure 4:
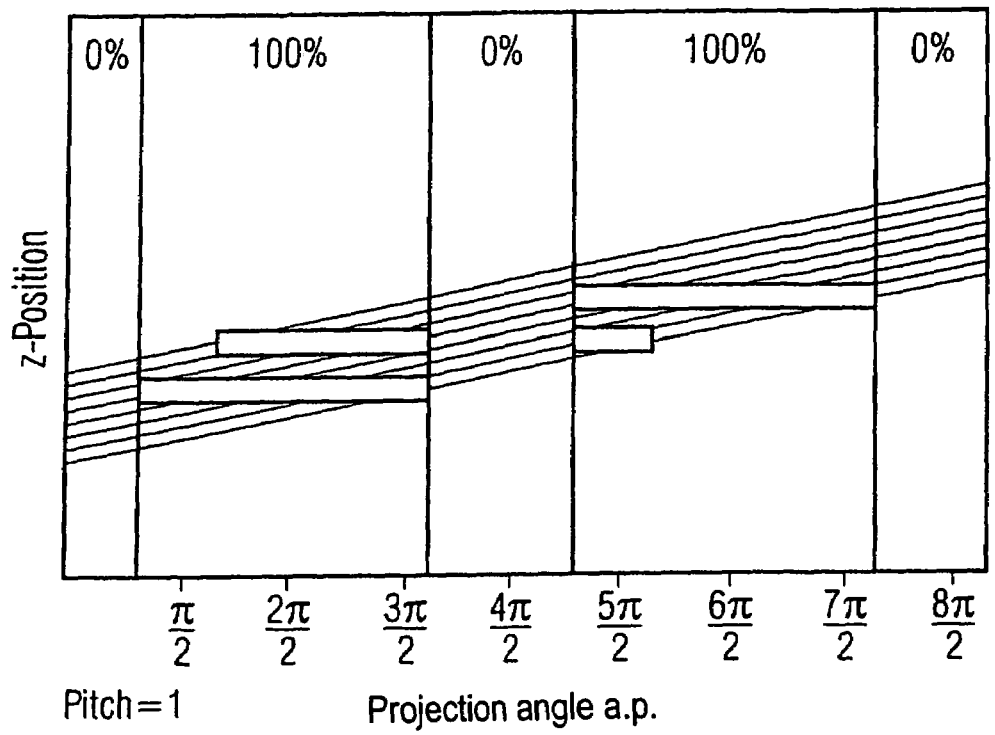
FIG. 4 schematically illustrates the data that the multi-row detector detects when the X-ray tube is switched on and the pitch factor is equal to 1.

FIGS. 3, 4 and 5 schematically show how the data recording takes place as a function of pitch. In each case, the projection angle is plotted with projection to the z position of the detector. FIG. 3 show which data the detector detects when the X-ray tube is switched on (100% range or rather radiation segment) for a pitch less than one and FIG. 4 for a pitch equal to one. For the a.p. projections $\beta = 180° - \alpha$, the tube current is switched off (0%). The pitch characterizes the detector course during the rotation. Each row 9 corresponds to the recorded data according to the course of a detector element of a detector row of a certain width. The steepness or slope of the row course is defined by the table feed. The pitch or pitch factor is characterized (as mentioned above) by the number and the width of the detector channels and by the table feed (along the z axis). If the pitch is equal to one or less than one (FIGS. 3 and 4), sufficient data are available in each z position under certain circumstances divided among the preceding and following 100% segment (radiation segment) in order to be able to reconstruct for this z position an image slice. A complete data set is symbolized in both figures (FIGS. 3 and 4) as a white bar. Particularly for a pitch p=1, for reconstruction of an image in case of data distribution to adjacent radiation segments a resorting must be performed.

FIG. 5 illustrates the data-recording situation for a pitch greater than one. Also for the z position 10, sufficient data are available (180°+fan angle) to reconstruct a complete image. For the reconstruction of an image for z position 11, however, this condition is not fulfilled since in the hatched region 12 no data were acquired. The projection data set for z position 11 is thus incomplete, but can be filled (supplemented) according to the method of the invention. To accomplish this, it is sufficient to compute the data for the hatched region in a preprocessing step. This can take place, for example, by (linear) interpolation between the nearest data points at the same projection angle (in the case of FIG. 5, the range about $7\pi/2$). Suitable data points can be found either in the same projection on a different row (black region 13) or also one 360° rotation before (black region 14) or after (not shown). After this preprocessing step, one can proceed as with the z position 10.

In summary, with the method according to the invention the radiation dose on the a.p. side of the patient can be reduced considerably. In particular, radiation-sensitive organs on the a.p. side such as the gonads, female mammary glands, the thyroid gland and the eye lens are greatly spared in this manner. The dose reduction according to the method according to the invention is considerably greater than a purely constant reduction of the mA value according to the prior art. Moreover, the effective dose for the patient is also reduced to a considerable extent (this indicates the total value weighted over all organs according to their radiation sensitivity in conformity with the internationally applicable recommendations (ICRP, 1990). In contrast to further dose-reduced techniques according to the prior art (such as HandCARE), the dose-reduced recording and reconstruction technique according to the invention in spiral mode allows a fast data acquisition technique for large volumes. The reconstruction methods allow the computation of images at arbitrary z positions for a wide variety of pitch values.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for reconstructing an incomplete projection data set in computed tomography, comprising the steps of:
    conducting a spiral scan along a z-axis of a subject on a table by moving said table along said z-axis while rotating a radiation source around the subject and emitting a penetrating radiation beam from the source to irradiate the subject from different rotational angles, at a pitch greater than or equal to one, and detecting penetrating radiation from said beam attenuated by the subject with a multi-row detector to obtain a plurality of projection data sets respectively for a plurality of z-positions along said z-axis;
    selectively reducing a radiation dose associated with said penetrating radiation beam when said radiation source is at at least one of said rotational angles, thereby causing at least one of said projection data sets to be an incomplete projection data set;
    completing said incomplete data set using completion data in said incomplete projection data set obtained from other rows of said multi-row detector or using completion data from a projection data set preceding said incomplete projection data set in said spiral scan or using completion data from a projection data set following said incomplete projection data set in said spiral scan; and
    reconstructing a multi-dimensional image of the subject from said projection data sets, including said completed incomplete projection data set.

2. A method as claimed in claim 1 comprising completing said incomplete projection data set by interpolating incomplete data in said incomplete projection data set using said completion data.

3. A method as claimed in claim 2 comprising linearly interpolating said incomplete projection data using said completion data.

4. A method as claimed in claim 1 wherein said pitch is equal to one and, for reconstructing an image of the subject at a z-position between two radiation segments, re-sorting data from rotations of said radiation source adjacent said z-position.

5. A method as claimed in claim 1 wherein the step of selective reducing said radiation dose comprises reducing said radiation dose at a location anterior of said subject, in an angular range of $\beta=180°-\alpha$, wherein $\alpha$ is a fan angle of said penetrating radiation beam.

6. A method as claimed in claim 1 comprising supplying said radiation source is an x-ray tube operating with a tube current to emit an x-ray beam as said penetrating radiation beam, and wherein the step of selectively reducing said radiation dose comprises switching off said tube current when said x-ray source is at said at least one angular position.

7. A computed tomography apparatus comprising:
- a computed tomography scanner including a movable patient table, a radiation source and a multi-row radiation detector for conducting a spiral scan along a z-axis of a subject on the table by moving said table along said z-axis while rotating said radiation source around the subject and emitting a penetrating radiation beam from the radiation source to irradiate the subject from different rotational angles, at a pitch greater than or equal to one, and for detecting penetrating radiation from said beam attenuated by the subject with the multi-row detector to obtain a plurality of projection data sets respectively for a plurality of z-positions along said z-axis;
- a control unit that selectively reduces a radiation dose associated with said radiation beam when said radiation source is at at least one of said rotational angles, thereby causing at least one of said projection data sets to be an incomplete projection data set;
- a computer that completes said incomplete data set using completion data in said incomplete projection data set obtained from other rows of said multi-row detector or using completion data from a projection data set preceding said incomplete projection data set in said spiral scan or using completion data from a projection data set following said incomplete projection data set in said spiral scan; and
- an image computer that reconstructs a multi-dimensional image of the subject from said projection data sets, including said completed incomplete projection data set.

8. A computer-readable medium encoded with a data structure, loadable into a computer of a computed tomography system, said data structure programming said computer to reconstruct an image from an incomplete projection data set among a plurality of projection data sets obtained by conducting a spiral scan along a z-axis of a subject on a table by moving said table along said z-axis while rotating a radiation source around the subject and emitting a penetrating radiation beam from the radiation source to irradiate the subject from different rotational angles, at a pitch greater than or equal to one, and detecting penetrating radiation from said beam attenuated by the subject with a multi-row detector to obtain a plurality of projection data sets respectively for said plurality of z-positions along said z-axis, and selectively reducing a radiation dose associated with said radiation beam when said radiation source is at at least one of said rotational angles, thereby causing at least one of said projection data sets to be an incomplete projection data set:
- said data structure causing said computer to complete said incomplete data set using completion data in said incomplete projection data set obtained from other rows of said multi-row detector or using completion data from a projection data set preceding said incomplete projection data set in said spiral scan or using completion data from a projection data set following said incomplete projection data set in said spiral scan, and to reconstruct a multi-dimensional image of the subject from said projection data sets, including said completed incomplete projection data set.

* * * * *